United States Patent
Ejlersen et al.

(10) Patent No.: US 8,409,140 B2
(45) Date of Patent: Apr. 2, 2013

(54) INJECTION APPARATUS

(75) Inventors: Henning Munk Ejlersen, Vedbaek (DK); Søren Aasmul, Holte (DK)

(73) Assignee: Medtronic Minimed, Inc., Northridge, CA (US)

( * ) Notice: Subject to any disclaimer, the term of this patent is extended or adjusted under 35 U.S.C. 154(b) by 241 days.

(21) Appl. No.: 12/673,849

(22) PCT Filed: Aug. 14, 2008

(86) PCT No.: PCT/EP2008/060662
§ 371 (c)(1),
(2), (4) Date: Feb. 17, 2010

(87) PCT Pub. No.: WO2009/024521
PCT Pub. Date: Feb. 26, 2009

(65) Prior Publication Data
US 2011/0046454 A1    Feb. 24, 2011

(30) Foreign Application Priority Data

Aug. 17, 2007  (GB) .................................... 0716159.9
Sep. 21, 2007  (GB) .................................... 0718488.0

(51) Int. Cl.
*A61M 5/00* (2006.01)
(52) U.S. Cl. ............................................. 604/117
(58) Field of Classification Search ............ 604/117, 604/187, 192, 198; 600/309
See application file for complete search history.

(56) References Cited

U.S. PATENT DOCUMENTS

| | | | |
|---|---|---|---|
| 2,716,983 A | 9/1955 | Windischman et al. | |
| 5,968,022 A | 10/1999 | Saito | |
| 6,994,691 B2 * | 2/2006 | Ejlersen | 604/117 |
| 2003/0171716 A1 | 9/2003 | Ejlersen | |
| 2006/0178646 A1 | 8/2006 | Harris et al. | |
| 2006/0211982 A1 | 9/2006 | Prestrelski et al. | |
| 2006/0276759 A1 | 12/2006 | Kinast et al. | |

FOREIGN PATENT DOCUMENTS

| | | |
|---|---|---|
| EP | 0 596 161 | 5/1994 |
| FR | 2 756 493 | 6/1998 |
| WO | WO 96/07397 A2 | 3/1996 |
| WO | WO 00/02048 | 1/2000 |
| WO | WO 02/30275 A1 | 4/2002 |
| WO | WO 2006/06127 A1 | 6/2006 |
| WO | WO 2006/061208 A1 | 6/2006 |

OTHER PUBLICATIONS

"Needles" brochure from www.harvardapparatus.com.
International Search Report for PCT/EP2008/060662, mailed Feb. 23, 2009.

* cited by examiner

Primary Examiner — Kevin C Sirmons
Assistant Examiner — Imani Hayman
(74) Attorney, Agent, or Firm — Nixon & Vanderhye, PC

(57) ABSTRACT

An injection apparatus for making an injection at a predetermined depth in skin comprises: a first skin positioning member, a second skin positioning member, wherein the first and second skin positioning members lie or are moveable to lie in an injection arrangement; an injection needle; and an injection needle movement guide to guide the injection needle for movement from a parking position above the skin, through the lower surface of the second skin positioning member to slide beneath the first skin positioning member to an injection position. A further injection apparatus comprises: an injection needle; a plunger within the injection needle; and a retractor to retract the injection needle such that material to be injected is expelled from the injection needle by the plunger.

20 Claims, 11 Drawing Sheets

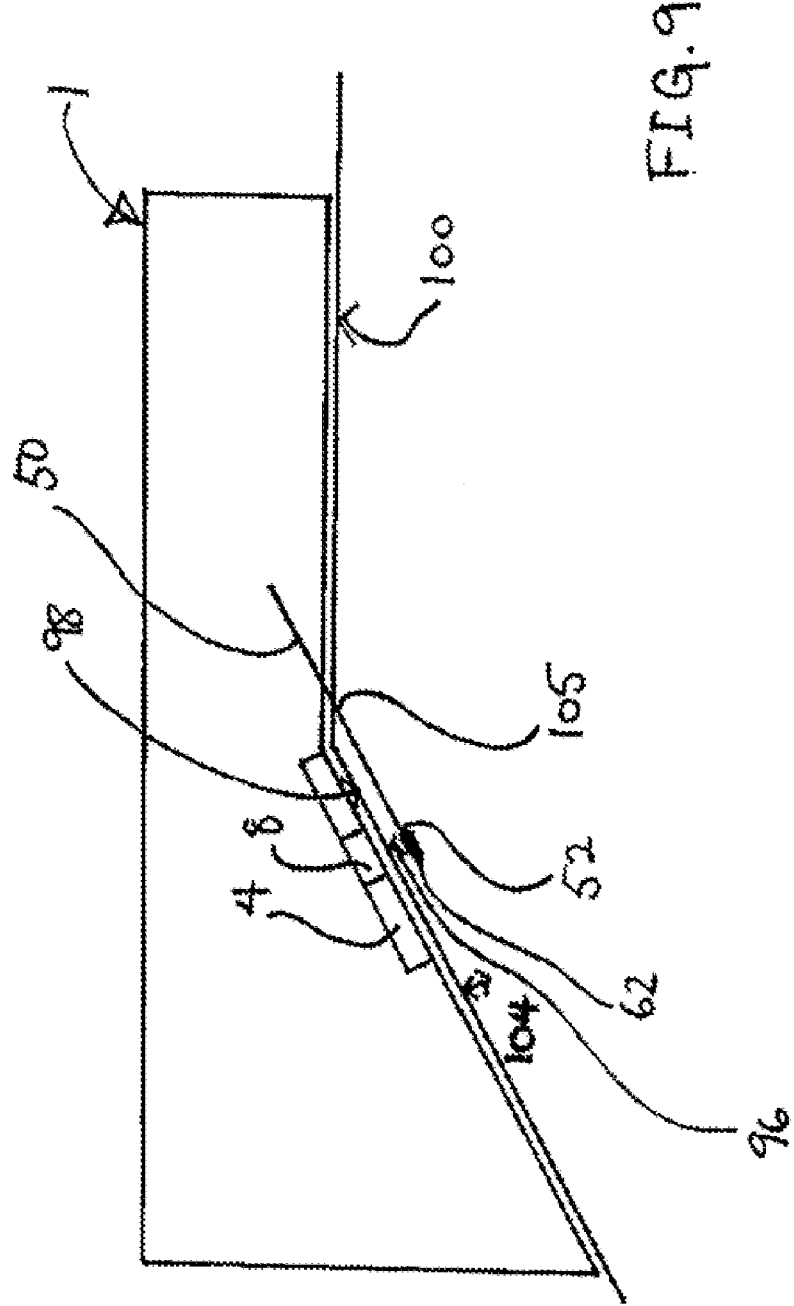

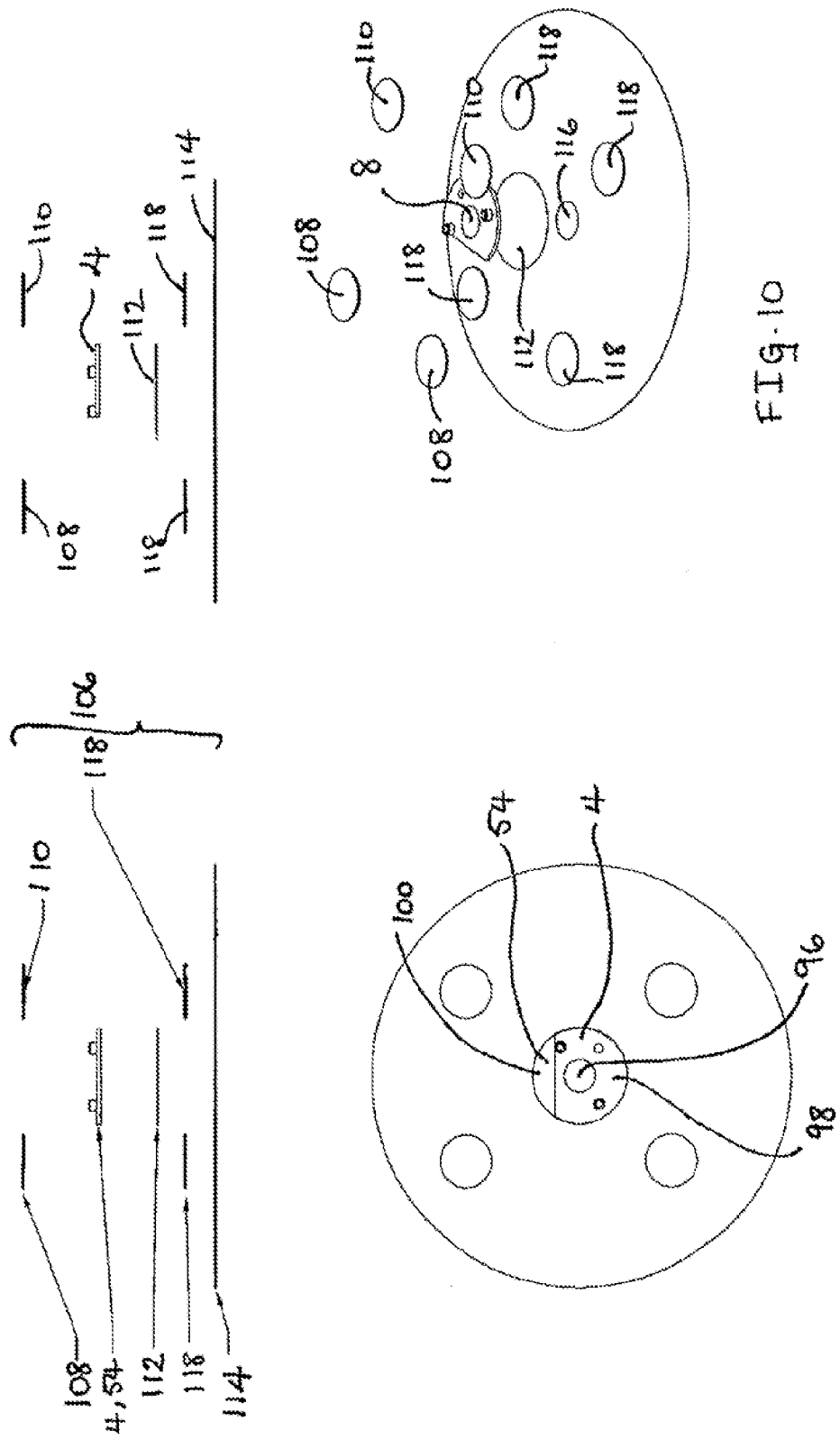

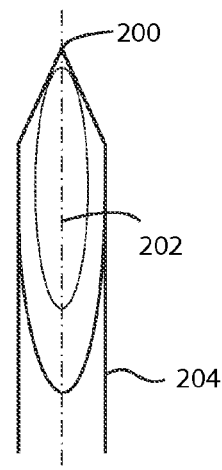
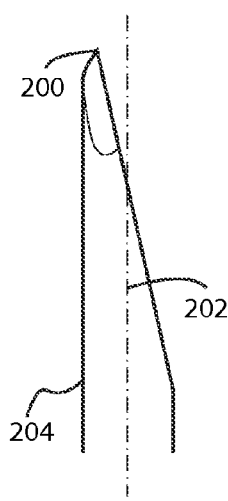
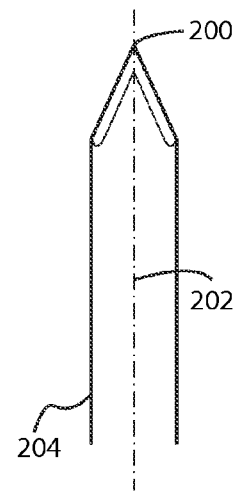
FIG. 11(a)     FIG. 11(b)     FIG. 11(c)
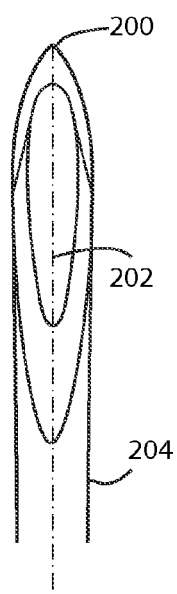
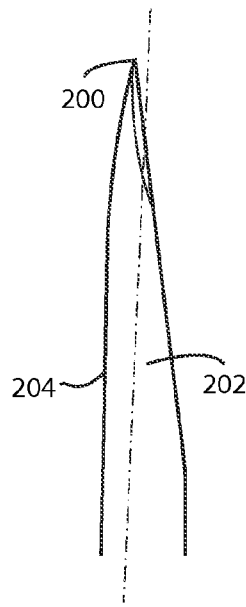
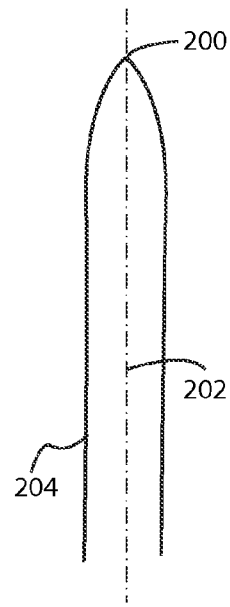
FIG. 12(a)     FIG. 12(b)     FIG. 12(c)
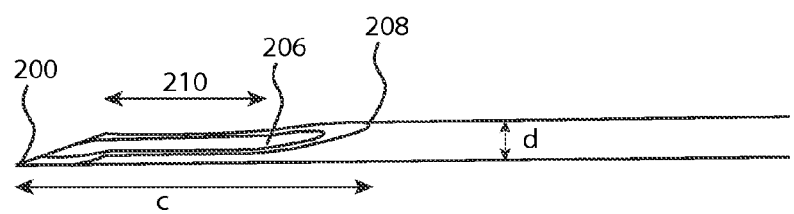
FIG. 13

INJECTION APPARATUS

This application is the U.S. national phase of International Application No. PCT/EP2008/060662 filed 14 Aug. 2008, which designated the U.S. and claims priority to GB Application No. 0716159.9 filed 17 Aug. 2007; and GB Application No. 0718488.0 filed 21 Sep. 2007, the entire contents of each of which are hereby incorporated by reference.

The present invention relates to an injection apparatus and to a method of injection.

Cutaneous injection is used in a number of applications. It is advantageous to inject vaccines into the skin as antigen which is then released into other tissues over a period of time, promoting the response by antibodies and T-cells. Assay sensors may also be injected into the skin, where they can be interrogated optically through the skin. Such assays are described for example in WO00/02048 and WO02/30275. They may in particular be useful for glucose monitoring in diabetes. Cutaneous injection is also used cosmetically in wrinkle filling.

The depth at which material is injected is important, as it determines the layer of the skin in which the material will be deposited. The skin consists of two principal layers: the epidermis (upper layer) and the dermis (lower layer), with an overall thickness of 1.5 to 2 mm. The epidermis is overlaid by the stratum corneum, a layer of dead cells approximately 10 to 25 μm thick. The upper cells of the stratum corneum are continuously worn away. The epidermis and dermis are separated by the basement membrane at a depth of approximately 150 μm. The cells at the top of the epidermis progressively die and form the base of the stratum corneum, whilst the basement membrane generates new cells at the base of the epidermis. The dermis is vasculised, whereas the epidermis is not.

The fluorophores commonly used in the competition assays referred to above are illuminated transdermally with blue or green light, which has a low penetration depth. Melanin, which absorbs UV and visible radiation, is produced by the basement membrane and transferred upwards into the epidermis to protect the skin from UV radiation. This melanin absorbs blue and green illumination used to interrogate the sensors and the resulting fluorescence, and accordingly penetration through the skin is poor. Absorption of light by blood contributes to this effect. Therefore, the deeper the sensors are positioned in the skin, the weaker the fluorescence detection will be. Accordingly, for optimum sensitivity of the assay, the sensors should be as close to the skin surface as possible.

However, there are disadvantages associated with positioning the reagent particles within the epidermis or basement membrane. In particular, the concentrations of glucose within these layers may not correlate with the blood glucose concentration which the assay is attempting to measure. This is because the epidermis is not vasculised, and the basement membrane uses glucose in the production of epidermal cells which affects its glucose concentration. By contrast, the concentration of glucose in the interstitial fluid of the dermis is expected to correlate with blood glucose concentration. Further, if the reagent particles were positioned in the epidermis, they would move towards the skin surface as the epidermal cells were renewed. Glucose concentration in the epidermis is known to decrease towards the skin surface (and is zero at the stratum corneum), and this would cause complications. Particles injected into the dermis, on the other hand, will be retained permanently, as seen in a conventional tattoo.

In the light of these considerations, the optimum location for assay reagent particles is directly underneath the basement membrane, at the top of the dermis.

In other assays, it may be desirable for sensor particles to be deposited in the epidermis so that they will be expelled from the body over time (WO02/30275). Shallow injection may be achieved using an array of short needles coated with material to be injected. However, when injection is carried out with an array of this type material is deposited at every depth from the skin surface to the maximum penetration depth of the needle.

An apparatus or method that provides injection to a predetermined depth is consequently desirable. Such an apparatus is described in WO03/072172.

In a first aspect, the present invention provides an injection apparatus for making an injection at a predetermined depth in skin comprising:
a first skin positioning member having a lower surface for positioning on a first patch of skin to hold the first patch of skin in a defined position;
a second skin positioning member having a lower surface for positioning on a second patch of skin to hold the second patch of skin in a defined position, wherein the first and second skin positioning members lie or are moveable to lie in an injection arrangement;
an injection needle having a discharge opening; and
means guiding the injection needle for movement from a parking position above the skin, through the lower surface of the second skin positioning member to enter the second patch of skin and to slide beneath the first skin positioning member to an injection position in which the discharge opening of the needle lies at a predetermined distance below the lower surface of the first skin positioning member.

Preferably, the injection needle is guided for movement of the discharge opening of the needle at a constant distance below the lower surface of the first skin positioning member (that is, parallel to the lower surface of the first skin positioning member). This will ensure that the injection depth is not dependent on the precise distance over which the injection needle is moved, as would be the case if the injection needle moved obliquely with respect to the first skin positioning member. In this embodiment, the lower surfaces of the first and second skin positioning members are typically non-parallel in the injection arrangement.

Preferably, the lower surface of the first skin positioning member and/or the lower surface of the second skin positioning member is at least substantially flat, so that the first patch of skin and/or the second patch of skin is at least substantially flat. However, non-flat skin positioning members may be used.

One or both of the first skin positioning member and the second skin positioning member may be plate-like, or may form the surface of a non-plate-like member, for example a cone, a pyramid, a triangular prism or a hemisphere.

Preferably, the lower surfaces of the first skin positioning member and the second skin positioning member form a concave arrangement in the injection arrangement. Where the lower surfaces of the first and second skin positioning members are flat, the angle between the lower surfaces will be less than 180° in a concave injection arrangement. The first and second patches of skin may be elevated above the surrounding area of skin, or one or both patches of skin may be at least partly depressed below the surrounding area of skin.

In a preferred embodiment, the first and second skin positioning members are moveable between a non-injection arrangement (in which they are typically co-planar) and an injection arrangement. However, the first skin positioning member and second skin positioning member may be fixed in the injection arrangement.

Preferably, the first skin positioning member and second skin positioning member are adjacent to one another, although they may alternatively be non-adjacent. More preferably, the first skin positioning member and second skin positioning member are adjacent along a shared edge.

Preferably, the first skin positioning member and the second skin positioning member are rotatably connected to one another, for example by means of one or more hinges.

Preferably, the injection apparatus comprises means for effecting relative movement (preferably rotation) of the first skin positioning member and the second skin positioning member between a non-injection arrangement and the injection arrangement. For example, the means may comprise a pivoted rod arrangement, or may comprise a box cam arrangement. Preferably, a manually engageable operating means, for example a slider, is provided.

Preferably, the injection apparatus comprises means for attaching the first skin positioning member to the first patch of skin and/or the second skin positioning member to the second patch of skin. As an alternative, however, one or both skin positioning members can be pressed against the skin.

More preferably, the means is adhesive, for example an adhesive coating or adhesive tape provided on the lower surface of the first skin positioning member and/or the second skin positioning member. Suitably, the adhesive is initially covered with a release tape which is removed in use.

Additionally or alternatively, one or both of the first skin positioning member and the second skin positioning member may be porous or provided with bores through which vacuum may be applied to hold the skin to the skin positioning member.

Additionally or alternatively, one or both of the first skin positioning member and the second skin positioning member may be provided with one element of a hook and loop fastening pair. The other element would need to be fastened to the skin, for example using adhesive.

In one preferred embodiment, the first skin positioning member and the second skin positioning member occupy at least substantially the whole lower surface of the injection apparatus. However, in an alternative preferred embodiment, the first skin positioning member and the second skin positioning member occupy only part of the lower surface of the injection device.

Preferably, the injection needle is guided for movement using a box cam arrangement, with a cam follower mounted to the injection needle engaging in a cam groove in a cam plate mounted for sliding movement with respect to the injection needle.

Preferably, the injection apparatus further comprises a plunger. More preferably, the plunger is guided for movement using a box cam arrangement, with a cam follower mounted to the plunger engaging in a cam groove in a cam plate mounted for sliding movement with respect to the plunger.

Suitably, a single cam plate with multiple cam grooves engages the cam followers of both the injection needle and the plunger.

Preferably, the injection needle and plunger are guided by the cam follower and cam plate for both advancement into the skin and retraction from the skin.

Preferably, the cam plate is provided with a manually engageable operating means, for example a slider.

In a preferred embodiment, the cam plate is initially locked against sliding movement and is released on relative movement of the first and second skin positioning members to the injection arrangement. This avoids injection accidentally taking place before the injection apparatus is in the injection arrangement, which would not necessarily be at the desired predetermined depth.

The predetermined depth is preferably in the range 100 μm to 2 mm, and may be fixed during manufacture or may be user adjustable within a certain range, for example using a dial coupled to a screw jack lifting the injection assembly. As explained above, injection directly below the basement membrane (depth approximately 150 μm) may be desirable.

Preferably, the injection needle contains a sensor to be injected. Suitably, the sensor contains assay reagents. Assays of particular interest are the competitive glucose assays described in WO06/061207 and WO06/061208. However, the injectable material in the syringe may alternatively be a medicament and may be an antigen for use in an immunisation.

Preferably, the injection apparatus comprises a lower portion which is left on skin after injection to define the injection site and an upper portion containing the injection needle which is detachable after injection.

More preferably, the lower portion contains a window or an aperture through which the sensor can be interrogated optically. Suitably, the maximum dimension of the window or aperture is 2 mm.

Preferably, the injection apparatus comprises means for locking the lower portion to the upper portion. In a preferred embodiment, the lower portion is released from the upper portion using a box cam arrangement, suitably using the same cam plate used to control movement of the injection needle and/or plunger.

Preferably, the lower portion forms at least part of the first skin positioning member. Preferably, the upper portion includes the second skin positioning member.

The injection needle may be of various types. Injection needle types such as a lancet type or trocar type needle are known.

An injection needle is generally formed from tubing having a lumen and a shaft, and a point is formed at the distal end of the needle by cutting across the tubing transversely to its longitudinal axis to form at least one bevel.

A lancet type needle may be formed by grinding a primary bevel at an angle to the longitudinal axis using a grinding stone then making secondary bevels by increasing the grinding angle and rotating the needle with respect to the grinding stone about the longitudinal axis of the needle to give two secondary bevels with equal and opposite rotations of less than 90°.

A trocar type needle may be formed by making three grindings to the needle: a first grinding to form a primary bevel as described above and two subsequent grindings with increased grinding angle to form secondary bevels with equal and opposite rotations of 120°.

Preferably, the injection needle is as described in co-pending United Kingdom Patent Application No. 0716159.9 of the same applicant and the PCT application claiming priority therefrom. These needles are designed for reliable insertion to the required depth in the skin.

It is desirable for the tip 200 of the injection needle to be closer to the longitudinal axis 202 of the shaft portion than is the outside of the shaft portion 204. This is suitably achieved either by grinding (FIG. 11) or by bending (FIG. 12) of the tip. A needle prepared by bending is commercially available as a Huber tip needle, for example from www.harvardapparatus.com.

Alternatively or additionally, it is desirable for the length l of the lumen opening 206 (extending from the tip 200 to the heel 208, i.e. the edge formed by the bevel surface meeting the outer surface of the shaft on the opposite side from the tip) of the needle to be in a range from 5 to 15 times the diameter d of the shaft of the needle (FIG. 13). Suitably at least a part 210 of the point is substantially parallel to the longitudinal axis of the needle to give a part-cylindrical (e.g. hemi-cylindrical) form.

In a second aspect, the invention relates to an injection apparatus comprising a plunger.

An apparatus for and method of injecting drugs in solid form into a patient's bloodstream is described in WO96/07397. In the apparatus described therein, a plunger is used to push a solid drug cylinder through a needle into the bloodstream.

The present inventors have found that when using a plunger to push a sensor through the needle of a device similar to that described in WO03/072172, the retraction of the injection needle and piston simultaneously may also cause retraction of the sensor from the desired injection location.

Accordingly, in its second aspect, the invention provides an injection apparatus comprising:
   an injection needle having a discharge opening;
   a plunger within the injection needle; and
   means for retracting the injection needle such that material to be injected is expelled from the discharge opening of the injection needle by the plunger.

Preferably, the injection apparatus further comprises means for advancing the injection needle, means for advancing the plunger and/or means for retracting the plunger. In a preferred embodiment, a releasable coupling is provided between the injection needle and plunger. In this way, the injection needle and plunger can be advanced together, the coupling released and the injection needle then retracted without retracting the plunger.

In a third aspect, the invention provides a method of cutaneous injection at a predetermined depth using an injection apparatus as described above, comprising:
   positioning the injection apparatus on the skin; and
   guiding the injection needle through the lower surface of the second skin positioning member to enter the second patch of skin and to slide beneath the lower surface of the first skin positioning member to bring the discharge opening of the injection needle to a predetermined depth beneath the lower surface of the first skin positioning member.

The method may further include a step of expelling the contents of the injection needle through the discharge opening.

The method may further include a step of effecting relative movement of the first and second skin positioning members into the injection arrangement after positioning the injection apparatus on the skin.

Suitably, the method can be carried out by a patient on himself/herself without the need for assistance from medical personnel.

Features described in connection with any aspect of the invention may be used in connection with any other aspect of the invention.

The invention will be further described with reference to the preferred embodiments shown in the accompanying drawings, in which:

FIG. 9 shows a simplified version of the view of FIG. 8, including the skin; and FIG. 10 shows exploded cross-sectional and perspective views of the means for mounting the injection apparatus of FIG. 1 to the skin both before the upper portion of the injection apparatus has been removed (left) and after the upper portion of the injection apparatus has been removed (right).

FIG. 11 shows an example of a trocar-type needle for use in the apparatus of the present invention. View (a) shows the primary bevel face of the needle, view (b) shows the needle rotated by 90° about its longitudinal axis compared with view (a), and view (c) shows the needle rotated by 180° about its longitudinal axis compared with view (a).

FIG. 12 shows an example of a lancet-type needle for use in the apparatus of the present invention. View (a) shows the primary bevel face of the needle, view (b) shows the needle rotated by 90° about its longitudinal axis compared with view (a), and view (c) shows the needle rotated by 180° about its longitudinal axis compared with view (a).

FIG. 13 shows a perspective view of another example of a needle for use in the apparatus of the present invention.

Figure 1:
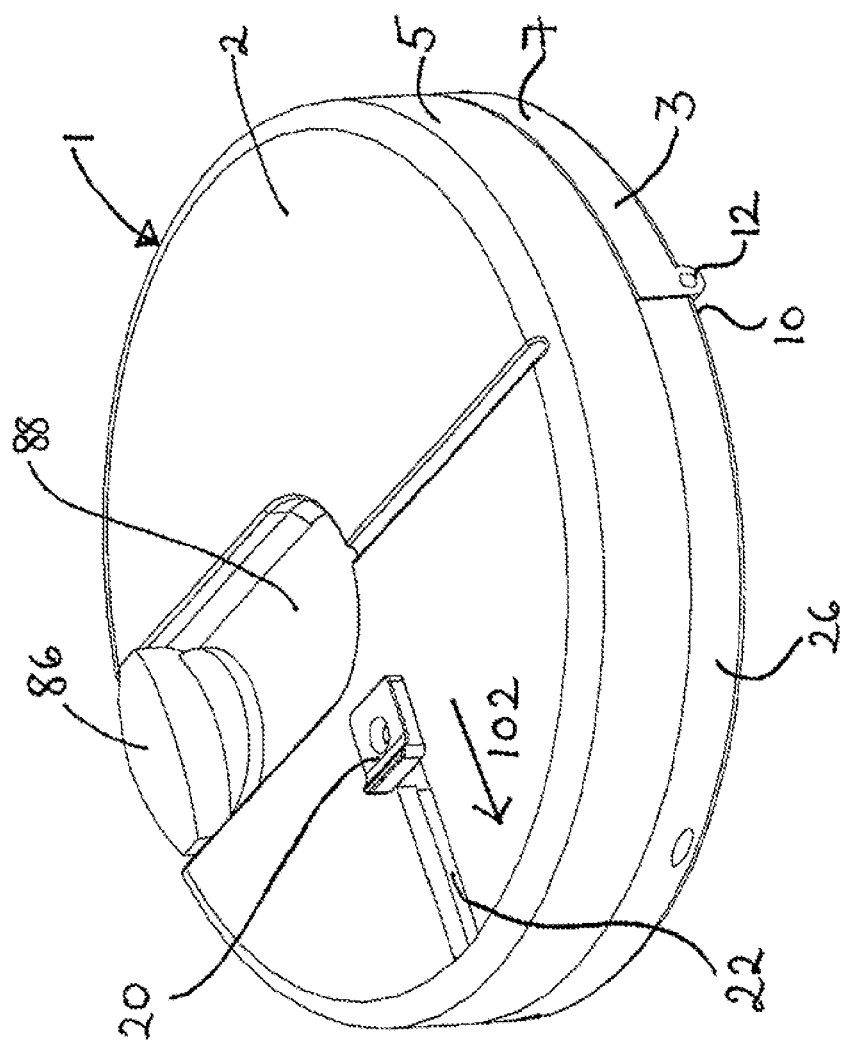
FIG. 1 shows a perspective view of a preferred embodiment of an injection apparatus of the invention.
Figure 2:
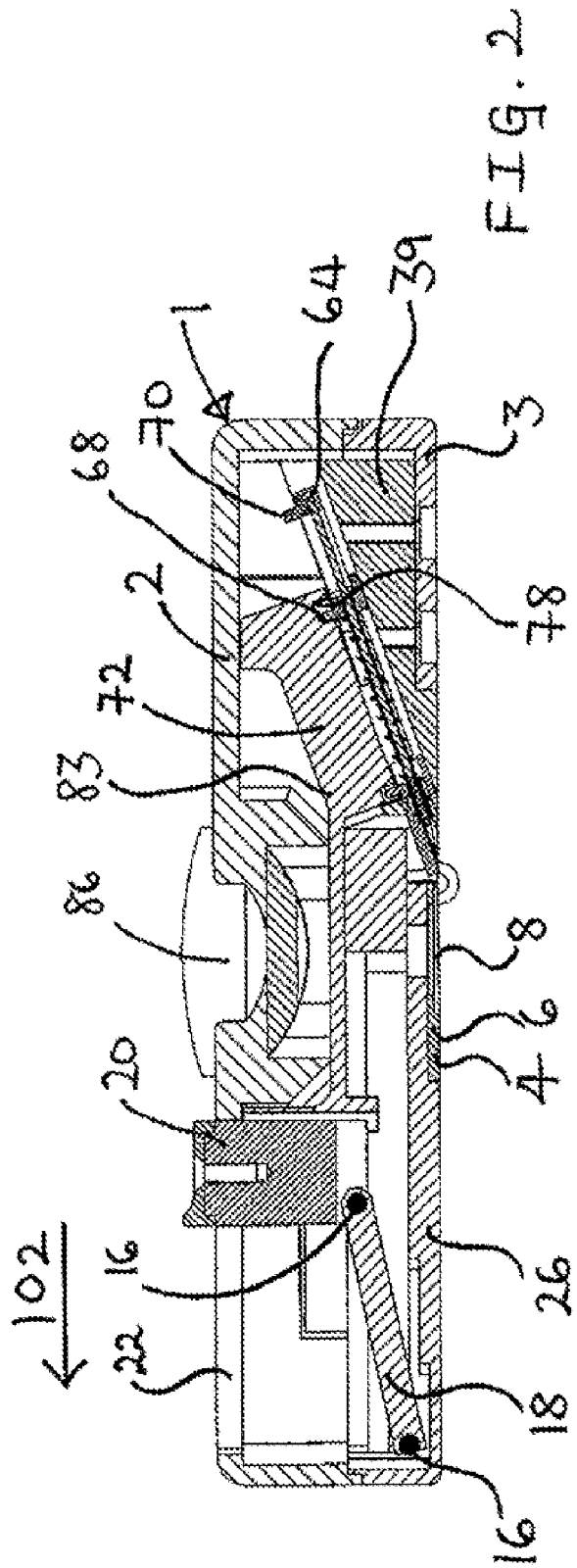
FIG. 2 shows a cross-sectional view of the injection apparatus of FIG. 1.

In a preferred embodiment of the present invention shown in the drawings, the injection apparatus 1 is generally circular cylindrical in shape and comprises an upper housing 2, a lower housing 3 and a hinged plate 26 (FIGS. 1 and 2).

The upper housing 2 is generally in the form of a circular top plate with a depending skirt 5. The lower housing 3 and hinged plate 26 together form a circular bottom plate with an upstanding skirt 7, which engages with depending skirt 5 via a snap fit. The lower housing and hinged plate 26 are hingedly connected to one another along edge 10 by hinges 12.

The lower housing 3 further comprises a circular support plate 14 which lies between the upper housing 2 and the hinged plate 26.

The hinged plate 26 is connected via pivots 16 and a rod 18 to a first manually engageable slider 20 mounted in a slot 22 in the top plate of the upper housing 2 (FIG. 2).

A marker 4 lies within the lower surface of hinged plate 26 adjacent to the edge 10. The marker 4 comprises a part-circular plate 6 having a central transparent window 8.

The lower housing 3 comprises an injecting assembly 36 (FIGS. 5 and 6) mounted in a sleeve 38 at an oblique angle (for example approximately 20°) to the circular support plate 14 of the lower housing 3. The sleeve 38 forms an integral part of a wedge shaped block 39. The sleeve 38 has an axial slot 41 on its upper surface.

Figure 5:
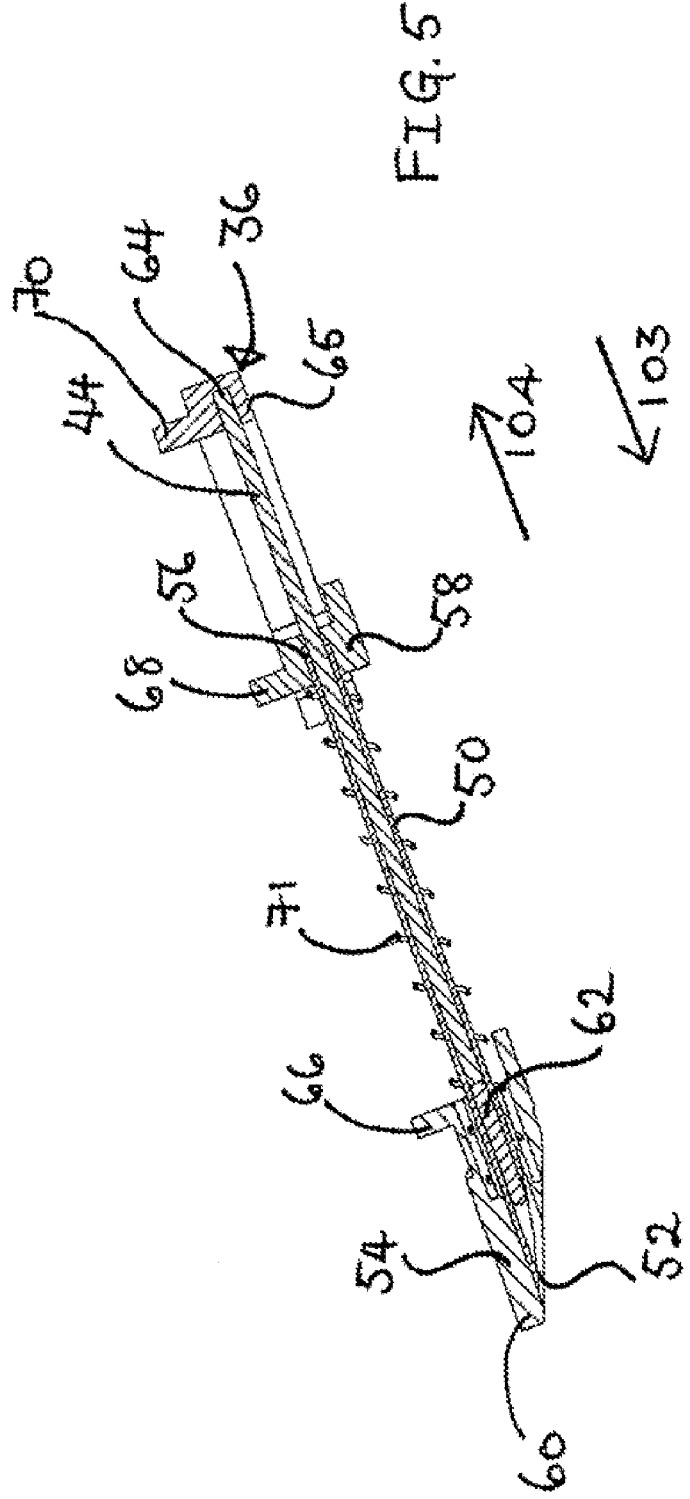
FIG. 5 shows a cross-sectional view of the injecting assembly of the injection apparatus of FIG. 1.

The injecting assembly 36 comprises a needle 50 having a discharge opening at its distal end 52. The needle 50 may be a lancet-type point needle wherein the distal end 52 (tip) is not closer to the longitudinal axis of the shaft than is the outside of the shaft (as shown in FIG. 5), or may alternatively be shaped as shown in any of FIGS. 11, 12 and 13. The needle 50 is supported at its distal end 52 (close to the centre of edge 10) within a central support block 54 and mounted at its proximal end 56 in a needle mounting block 58.

Figure 4:
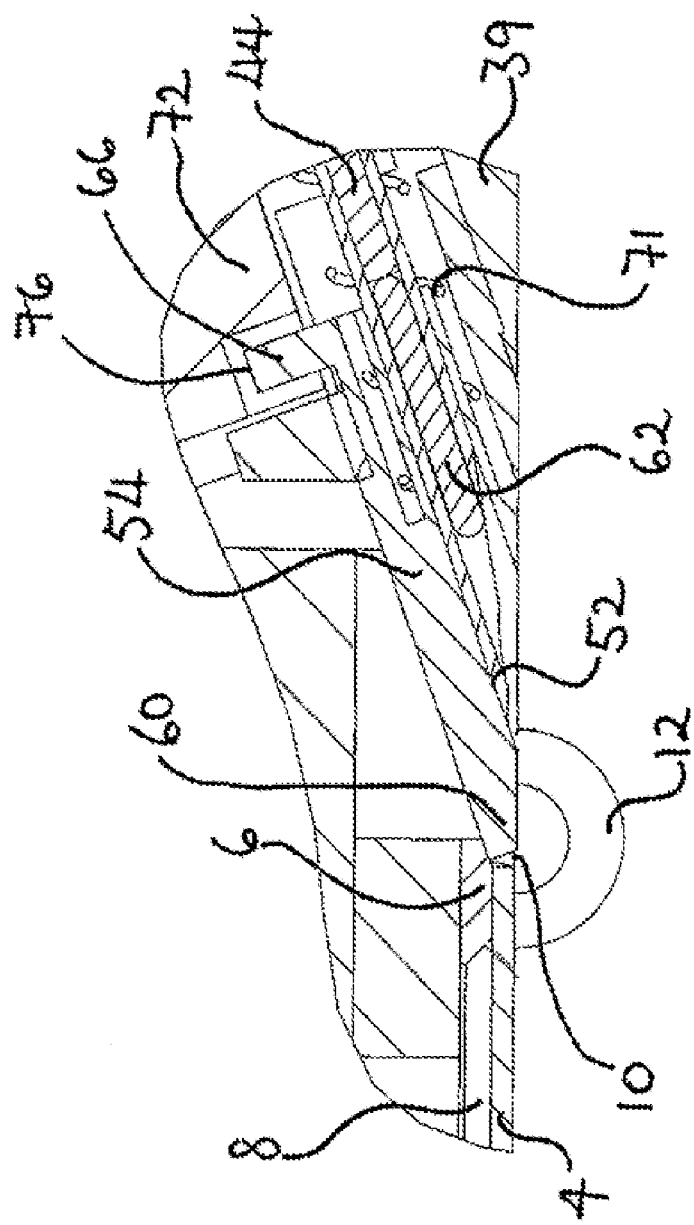
FIG. 4 shows an enlarged view of the central part of FIG. 2.

The central support block 54 has a tip 60 which engages the lower surface of the marker 4 to hold it in position (FIG. 4).

Figure 6:
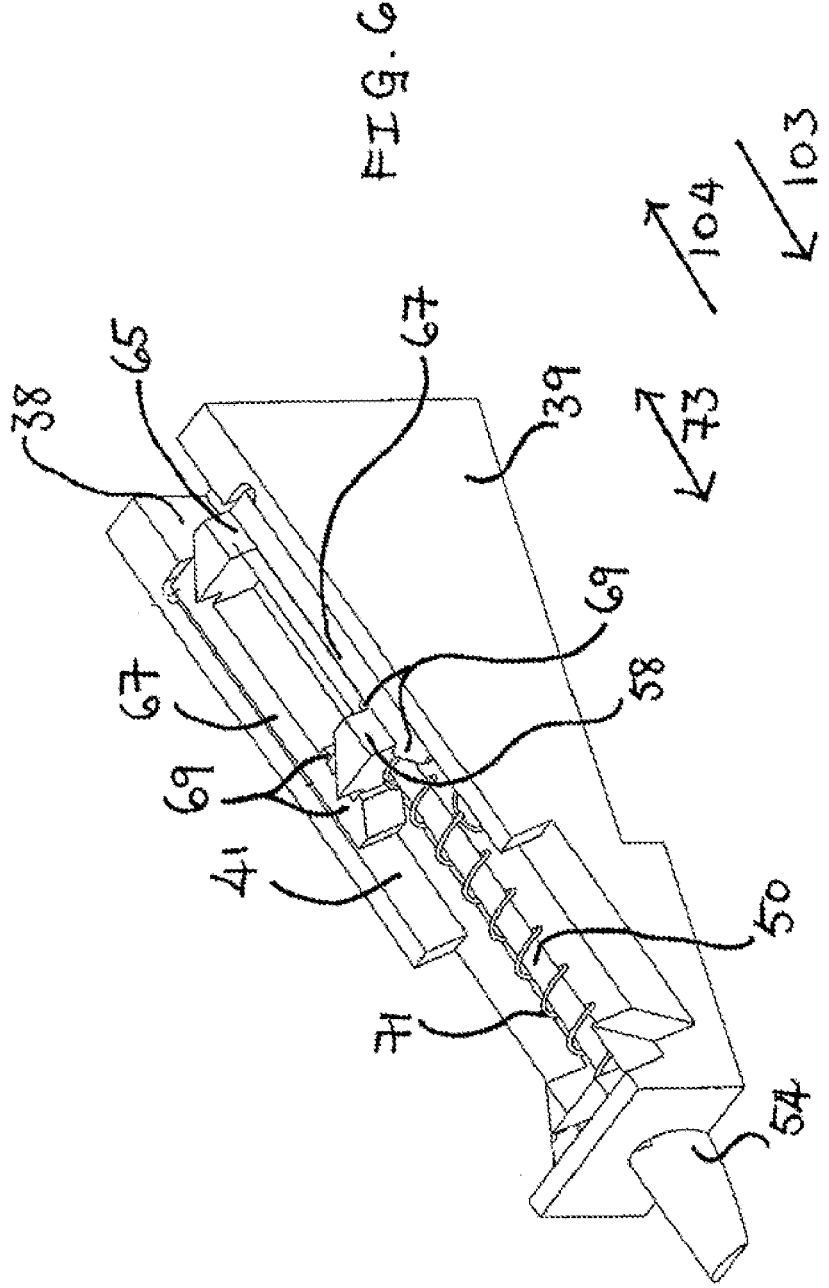
FIG. 6 shows a perspective view of the injecting assembly of FIG. 5.

A sensor 62 to be injected is positioned within the needle 50 at its distal end 52. A plunger 44 extends from behind the sensor 62 through the needle 50 and beyond the proximal end 56 of the needle 50. The plunger 44 is mounted at its proximal end 64 in a plunger mounting block 65. The plunger mounting block 65 extends into arms 67 which surround the needle mounting block 58 (FIG. 6). The arms 67 have internal ribs 69 which prevent axial movement of the needle mounting block 58 along the arms 67. A spring 71 surrounds the needle 50 and is compressed between the central support block 54 and the needle mounting block 58.

Cam followers 66, 68, 70 are provided on the central support block 54, the needle mounting block 58 and the plunger mounting block 65 respectively and protrude through the slot 41 in the sleeve 38. Each of the cam followers 66, 68, 70 is constrained by the slot 41 to movement in the direction 73.

Figure 7:
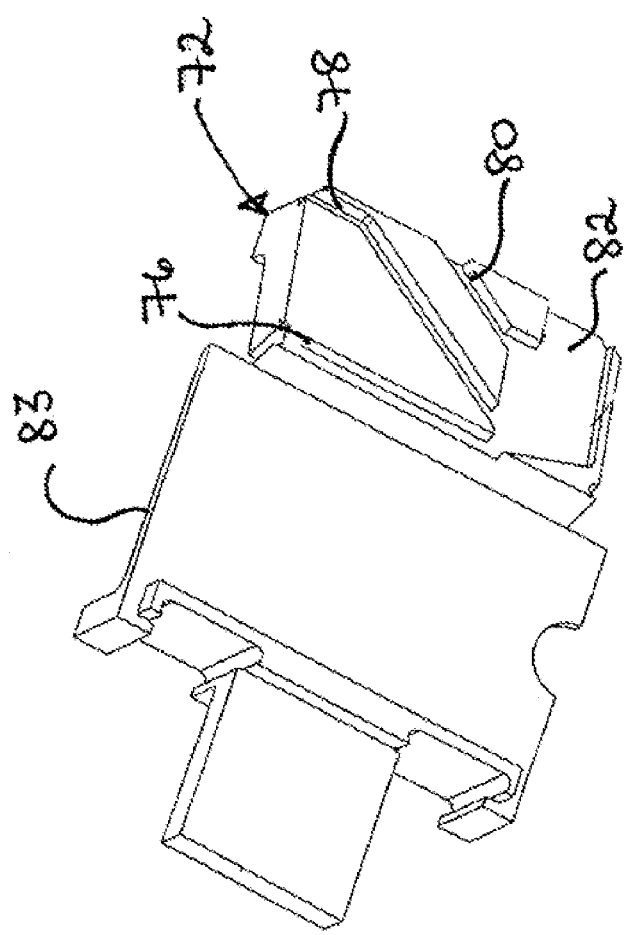
FIG. 7 shows a perspective view from below of the cam plate of the injection apparatus of FIG. 1.

A grooved cam plate 72 engages the cam followers 66, 68, 70 to form a box cam (FIG. 7). A cam groove 76 engaging cam follower 66 is perpendicular to slot 41 for most of its length and then angled outwards towards the periphery of the injection apparatus 1. A cam groove 78 engaging cam follower 68 is initially perpendicular to slot 41 and then angled inwards towards the centre of the injection apparatus 1. A cam groove 80 starts part way along the cam plate 72 and is initially parallel to the angled part of cam groove 78 and then is perpendicular to slot 41. The cam grooves 76, 78, 80 engaging cam followers 66, 68, 70 terminate in a common lateral cam groove 82 which is parallel to slot 41.

The cam plate 72 is mounted in slots 84 in the circular support plate 14 such that it is constrained to slide in directions 85 only. The cam plate 72 is provided on its upper surface 73 with a second manually engageable slider 86 which is mounted within a slot 88 on the upper surface of the upper housing 2.

Figure 3:
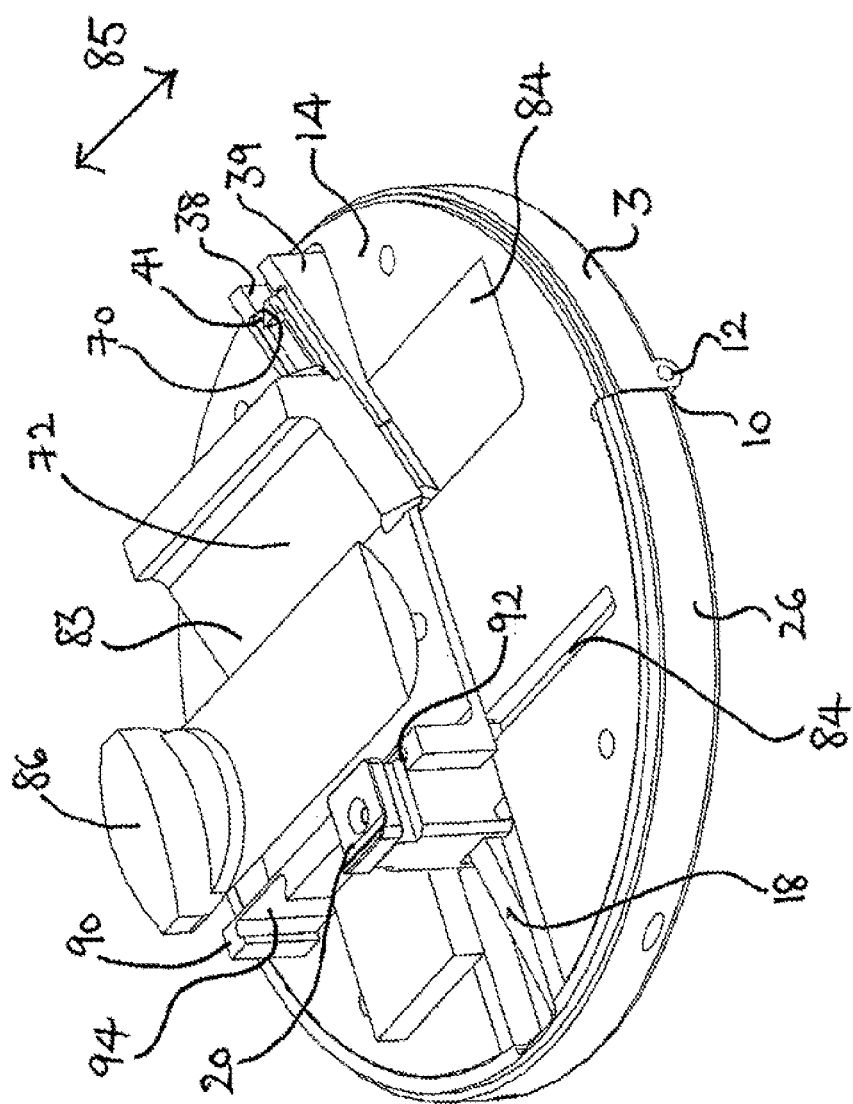
FIG. 3 shows a perspective view of the injection apparatus of FIG. 1 with upper housing removed.

Adjacent to the second manually engageable slider 86 on the side remote from the cam grooves, the cam plate 72 extends upwards to form a wall 90 (FIG. 3). The wall 90 contains two recesses 92, 94, one at each end, on the side remote from the second manually engageable slider 86. Recess 92 engages the first manually engageable slider 20.

The injection apparatus 1 is provided with means 106 for mounting to the skin (FIG. 10).

Means 106 for mounting the injection apparatus 1 to the skin comprises a tape disc 114 of diameter similar to that of the injection apparatus 1. The tape disc 114 is provided on its lower surface with an adhesive covering (not shown) covered by a release tape (not shown). The upper surface of the tape disc 114 is non-adhesive. The tape disc 114 has a central hole 116. The tape disc 114 has a further small hole (not shown) corresponding to needle entry point 105 (FIG. 9).

The looped discs 118 of each of four hook and loop fastening disc pairs are adhesively attached to the upper surface of the tape disc 114.

Complementary hooked discs 108 of each of two of the hook and loop fastening disc pairs are adhesively attached to the lower surface of the lower housing 3 of the injection apparatus 1. Complementary hooked discs 110 of the other two hook and loop fastening disc pairs are adhesively attached to the lower surface of the hinged plate 26 of the injection apparatus 1. The injection apparatus 1 is thus fastened to the tape disc 114 via the four hook and loop fastening disc pairs.

The lower surfaces of the marker 4 and the central support block 54 are attached to the central upper surface of the tape disc 114 with a transparent double sided tape disc 112. The window 8 in the marker 4 is aligned with the hole 116 in the tape disc 114. The double sided tape disc 112 has a small hole (not shown) aligned with the small hole in tape disc 114.

In use, the release tape is removed from the adhesive covering of the lower surface of the tape disc 114. The adhesive lower surface of the tape disc 114 is applied to the skin, adhering to an annular area of skin. Part of tape disc 114 attached to the marker 4 becomes adhesively attached to an area of skin 98, and part of tape disc 114 attached to the central support block 54 becomes adhesively attached to an adjacent area of skin 100. The part of double sided tape disc 112 aligned with hole 116 in tape disc 114 becomes adhesively attached to a circular area of skin 96.

Figure 8:
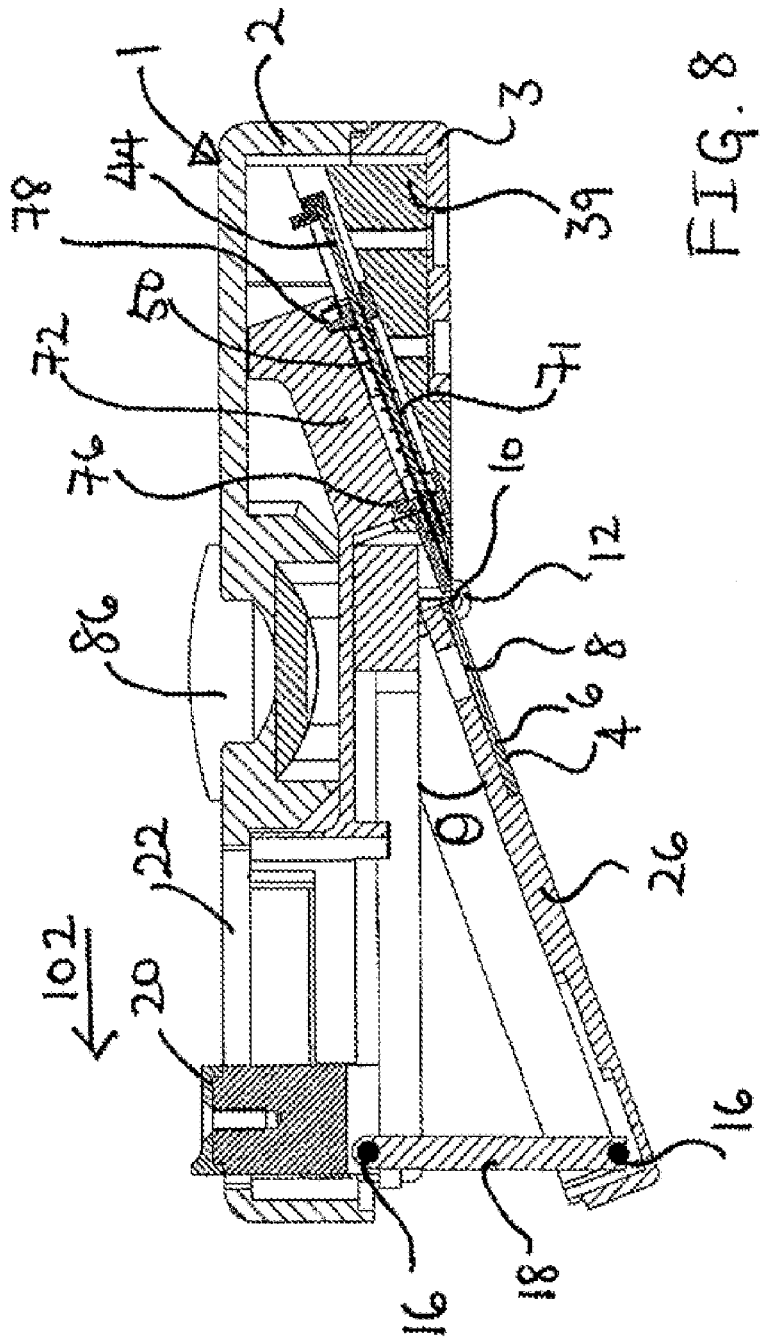
FIG. 8 shows a cross-sectional view of the injection apparatus of FIG. 1 during use.

To position injection apparatus 1 in its injection arrangement and to release the second manually engageable slider 86, the first manually engageable slider 20 is pushed along the slot 22 in direction 102 by the user. This causes rotation of rod 18 about pivots 16 such that the rod 18 extends downwards and rotates the hinged plate 26 around hinges 12, depressing the area of skin 96/98 through an angle θ (approximately 20°) such that the area of skin 96/98 lies parallel to the needle 50 (FIG. 8).

Movement of the first manually engageable slider 20 away from recess 92 in wall 90 also releases cam plate 72 such that it is slideable in slots 84.

To effect injection, the second manually engageable slider 86 is pushed along the slot 88 by the user. This causes the cam plate 72 to move along the slots 84 from its initial position shown in FIG. 3 to a final position. As the cam plate 72 moves, the cam follower 68 of the needle mounting block 58 is moved in direction 103 by cam groove 78. This causes the needle mounting block 58 and the injection needle 50 to move in direction 103 (parallel to the surface of the area of skin 96/98).

The distal end 52 of the needle 50 passes through the small holes in tape discs 112 and 114 and then through the surface of the area of skin 100 at needle entry point 105 to an injection position.

In the injection position the distal end 52 of the needle 50 is:
  below the surface of the area of skin 96 beneath the window 8 of the marker 4 (near the centre of the injection apparatus 1); and
  at a defined distance (defined depth in the skin) 104 from the surface of the area of skin 96.

Marker 4 and hinged plate 26 act as the first skin positioning member. Central support block 54 and the lower surface of lower housing 3 act as the second skin positioning member.

Because the needle mounting block 58 and plunger mounting block 65 are coupled by the arms 67 and ribs 69, the plunger 44 moves in direction 103 with the needle 50 and the cam follower 70 of the plunger mounting block 65 enters cam groove 80.

As the cam plate 72 moves further, the cam follower 68 of the needle mounting block 58 reaches the end of cam groove 78 and enters lateral cam groove 82. The spring 71, forming part of a retractor, forces the needle mounting block 58 away from the central support block 54, in direction 104, retracting the needle 50 from the skin. Cam follower 70 is restrained by cam groove 80 and therefore the plunger mounting block 65 and plunger 44 cannot move in direction 104. The needle mounting block 58 is forced past the ribs 69 in the arms 67 so that the needle mounting block 58 contacts the plunger mounting block 65. Thus, the coupling between the injection needle 50 and plunger 44 is released.

Retraction of the needle 50 has the effect that the sensor 52 is expelled by the plunger 44 from the distal end 52 of the needle 50 into the skin.

As the cam plate 72 moves still further, the cam follower 66 of the central support block 54 is moved in direction 104 by groove 76. Thus, the central support block 54 moves out of contact with double sided tape disc 112. The tip 60 of central support block 54 no longer engages the lower surface of the marker 4 and the marker 4 is thus released from the rest of the injection apparatus 1.

As the cam plate 72 continues to move, the cam follower 70 of the plunger mounting block 65 reaches the end of cam groove 80 and enters lateral groove 82. The spring 71 forces the plunger mounting block 65 in direction 104, retracting the plunger 44 from the skin.

At the end of the cam plate 72's path, the first manually engageable slider 20 can be returned along slot 22, where it engages recess 94 and prevents further movement of the cam plate 72 or second manually engageable slider 86.

The injection apparatus 1 can then be removed from the skin by disconnecting the four hook and loop fastening disc pairs. Tape disc 114 remains adhesively attached to the skin.

Marker 4 remains adhesively attached to the area of skin 96 and adhesively attached via double sided tape disc 112 to the area of skin 98, desirably for up to 14 days. Its central window 8 is used to define the site of the sensor 62. This may be important, for example in the injection of assays which need to be interrogated optically or otherwise at the site of injection.

The preferred embodiment of the injection apparatus allows injection to a fixed depth to be achieved accurately. The system has several advantages. First, as the needle extends under the skin surface the site of entry of the needle is not near the site of injection. This may be important in optical interrogation of assays. Secondly, the channel depth of the needle in the skin is much larger than the injection depth. This means that a seal is formed between the skin and the needle, so that the material to be injected does not travel along the outside of the needle to the outside of the skin. Thirdly, injected material is often spread out because of the pressure of injection and the possibility of migration through tissue. This is particularly significant in vertical injection into the skin, where material often reaches the fat tissue below the skin which has a low resistance to flow. Using the present injection apparatus, even if the injected material is spread out, it will be spread horizontally at the same depth. When the apparatus is used to inject assay sensors, this has the advantage that there is no stray signal from sensors at depths other than the required depth.

The preferred embodiment of the invention has a further advantage compared with the injection apparatus of WO03/072172.

As explained above, area of skin 96/98 is adhesively attached to the hinged plate 26 and marker 4 and area of skin 100 is adhesively attached to the lower surface of the lower housing 3. The injection needle 50 enters the skin at needle entry point 105 within area of skin 100. Thus, the area of skin 100 containing the needle entry point 105 is supported in a defined position during injection.

This is in contrast to the arrangement of WO03/072172, wherein only the area of skin over the distal end of the needle in the injection position is supported in a defined position (by means of an adhesive plate). The needle entry point lies within an area of skin which is not supported in a defined position during injection.

Tension within this unsupported area of skin and pressure as the needle contacts the skin both act to pull the supported area of skin (corresponding to area of skin 96/98) away from the adhesive plate. This can have the effect that injection does not reliably take place at the required depth, or even that the needle does not enter the skin at all.

The use of a large second skin positioning member is also of assistance in minimising tension in the area of skin containing the needle entry point.

The provision of small holes in the tape layers over the needle entry point allows undesirable introduction of adhesive into the skin to be avoided.

Expelling the sensor by retracting the injection needle while leaving the plunger extended has the advantage that undesirable retraction of the sensor from the desired injection location is avoided.

Where a needle as shown in any one of FIGS. 11, 12 and 13 is used, the depth of injection can be particularly reliably reproduced even for a sensor 62 requiring a large lumen diameter needle (e.g. 1.5 mm, large compared with the thickness of the skin). By contrast, using a conventional lancet-type point needle, the sensor may be injected too deeply when using the needle with the primary bevel facing away from the skin surface, or the needle may slide over the skin without penetrating the surface when using the needle with the primary bevel facing towards the skin surface. When a needle as shown in FIG. 13 is used, an additional benefit is that there is a reduction of the stress and lesions in the dermis caused by the insertion of the needle compared with that caused by a conventional needle.

Whilst the invention has been described with reference to the illustrated preferred embodiments, it is to be appreciated that many modifications and variations are possible within the scope of the invention.

The invention claimed is:

1. An injection apparatus for making an injection at a predetermined depth in skin comprising:
    a first skin positioning member having a lower surface for positioning on a first patch of skin to hold the first patch of skin in a defined position;
    a second skin positioning member having a lower surface for positioning on a second patch of skin to hold the second patch of skin in a defined position, wherein the first and second skin positioning members lie or are moveable to lie in an injection arrangement;
    an injection needle having a discharge opening;
    an injection needle movement guide to guide the injection needle for movement from a parking position above the skin, through the lower surface of the second skin positioning member to enter the second patch of skin and to slide beneath the first skin positioning member to an injection position in which the discharge opening of the needle lies at a predetermined distance below the lower surface of the first skin positioning member;
    a plunger within the injection needle; and
    a retractor to retract the injection needle such that material to be injected is expelled from the discharge opening of the injection needle by the plunger.

2. An injection apparatus as claimed in claim 1, wherein the injection needle is guided for movement of the discharge opening of the needle at a constant distance below the lower surface of the first skin positioning member.

3. An injection apparatus as claimed in claim 1, wherein the first skin positioning member holds the first patch of skin at least substantially flat and/or the second skin positioning member holds the second patch of skin at least substantially flat.

4. An injection apparatus as claimed in claim 1, wherein in the injection arrangement the lower surfaces of the first skin positioning member and the second skin positioning member form a concave arrangement.

5. An injection apparatus as claimed in claim 1, wherein the first skin positioning member and second skin positioning member are adjacent to one another.

6. An injection apparatus as claimed in claim 1, wherein the first skin positioning member and the second skin positioning member are rotatably connected to one another.

7. An injection apparatus as claimed in claim 1, further comprising an actuator to effect relative movement of the first skin positioning member and the second skin positioning member.

8. An injection apparatus as claimed in claim 1, further comprising an attachment member to attach the first skin positioning member to the first patch of skin and/or the second skin positioning member to the second patch of skin.

9. An injection apparatus as claimed in claim 8, wherein the attachment member is adhesive.

10. An injection apparatus as claimed in claim 1, wherein the injection needle is guided for movement using a cam follower mounted to the injection needle engaging in a cam groove in a cam plate mounted for sliding movement with respect to the injection needle.

11. An injection apparatus as claimed in claim 1, wherein the plunger is guided for movement using a cam follower mounted to the plunger engaging in a cam groove in a cam plate mounted for sliding movement with respect to the plunger.

12. An injection apparatus as claimed in claim 1, wherein the predetermined depth is user adjustable.

13. An injection apparatus as claimed in claim 1, wherein the injection needle contains a sensor to be injected.

14. An injection apparatus as claimed in claim 1, comprising a lower portion which is left on the skin after injection to define the injection site and an upper portion containing the injection needle which is detachable after injection.

15. An injection apparatus as claimed in claim 14, further comprising a release member to release the lower portion from the upper portion after injection.

16. A method of cutaneous injection at a predetermined depth using an injection apparatus as claimed in claim 1 comprising:
   positioning the injection apparatus on the skin; and
   guiding the injection needle through the lower surface of the second skin positioning member to enter the second patch of skin and to slide beneath the lower surface of the first skin positioning member to bring the discharge opening of the injection needle to a predetermined depth beneath the lower surface of the first skin positioning member.

17. An injection apparatus for making an injection at a predetermined depth in skin comprising:
   a first skin positioning member having a lower surface for positioning on a first patch of skin to hold the first patch of skin in a defined position;
   a second skin positioning member having a lower surface for positioning on a second patch of skin to hold the second patch of skin in a defined position, wherein the first and second skin positioning members lie or are moveable to lie in an injection arrangement;
   an injection needle having a discharge opening;
   an injection needle movement guide to guide the injection needle for movement from a parking position above the skin, through the lower surface of the second skin positioning member to enter the second patch of skin and to slide beneath the first skin positioning member to an injection position in which the discharge opening of the needle lies at a predetermined distance below the lower surface of the first skin positioning member;
   wherein the injection needle is guided for movement using a cam follower mounted to the injection needle engaging in a cam groove in a cam plate mounted for sliding movement with respect to the injection needle,
   wherein the cam plate is initially locked against sliding movement and is released on relative movement of the first and second skin positioning members to the injection arrangement.

18. An injection apparatus for making an injection at a predetermined depth in skin comprising:
   a first skin positioning member having a lower surface for positioning on a first patch of skin to hold the first patch of skin in a defined position;
   a second skin positioning member having a lower surface for positioning on a second patch of skin to hold the second patch of skin in a defined position, wherein the first and second skin positioning members lie or are moveable to lie in an injection arrangement;
   an injection needle having a discharge opening;
   an injection needle movement guide to guide the injection needle for movement from a parking position above the skin through the lower surface of the second skin positioning member to enter the second patch of skin and to slide beneath the first skin positioning member to an injection position in which the discharge opening of the needle lies at a predetermined distance below the lower surface of the first skin positioning member;
   further comprising a plunger,
   wherein the plunger is guided for movement using a cam follower mounted to the plunger engaging in a cam groove in a cam plate mounted for sliding movement with respect to the plunger,
   wherein the cam plate is initially locked against sliding movement and is released on relative movement of the first and second skin positioning members to the injection arrangement.

19. An injection apparatus for making an injection at a predetermined depth in skin comprising:
   a first skin positioning member having a lower surface for positioning on a first patch of skin to hold the first patch of skin in a defined position;
   a second skin positioning member having a lower surface for positioning on a second patch of skin to hold the second patch of skin in a defined position, wherein the first and second skin positioning members lie or are moveable to lie in an injection arrangement;
   an injection needle having a discharge opening;
   an injection needle movement guide to guide the injection needle for movement from a parking position above the skin, through the lower surface of the second skin positioning member to enter the second patch of skin and to slide beneath the first skin positioning member to an injection position in which the discharge opening of the needle lies at a predetermined distance below the lower surface of the first skin positioning member,
   wherein the injection needle comprises a point having a tip at a distal end thereof and a shaft portion immediately proximal to said point, the shaft portion having a longitudinal axis, the tip of the injection needle being closer to the longitudinal axis of the shaft portion than is the outside of the shaft portion.

20. An injection apparatus for making an injection at a predetermined depth in skin comprising:
   a first skin positioning member having a lower surface for positioning on a first patch of skin to hold the first patch of skin in a defined position;

a second skin positioning member having a lower surface for positioning on a second patch of skin to hold the second patch of skin in a defined position, wherein the first and second skin positioning members lie or are moveable to lie in an injection arrangement;

an injection needle having a discharge opening; and an injection needle movement guide to guide the injection needle for movement from a parking position above the skin, through the lower surface of the second skin positioning member to enter the second patch of skin and to slide beneath the first skin positioning member to an injection position in which the discharge opening of the needle lies at a predetermined distance below the lower surface of the first skin positioning member, wherein the injection needle comprises a tip, at least one bevel and a heel together forming a point at a distal end thereof, and a shaft portion immediately proximal of said heel having a longitudinal axis, including a lumen extending along the longitudinal axis, wherein the at least one bevel is formed between said tip and said heel such that a lumen opening is defined from the tip to a proximal end of the lumen opening located distal of the heel, and wherein the length of the lumen opening of the needle is in a range from 5 to 15 times the diameter of the shaft of the needle.

* * * * *